United States Patent [19]

Sweren et al.

[11] Patent Number: 4,770,171

[45] Date of Patent: Sep. 13, 1988

[54] CRYOGENIC SURGICAL TOOL

[76] Inventors: Ronald J. Sweren, 17 Farmhouse Ct., Baltimore; Alan Schwartz, 7 Pomona North #1, Pikesville, both of Md. 21208

[21] Appl. No.: 13,949

[22] Filed: Feb. 12, 1987

[51] Int. Cl.$^4$ .............................................. A61B 17/36
[52] U.S. Cl. ................................................. 128/303.1
[58] Field of Search ............... 128/303 R, 303.1, 399, 128/400, DIG. 27; 604/1–3

[56] References Cited

U.S. PATENT DOCUMENTS

| | | | |
|---|---|---|---|
| 1,705,256 | 3/1929 | Krusi | 604/2 |
| 3,421,508 | 1/1969 | Nestrock | 128/303.1 |
| 3,519,364 | 7/1970 | Truhan | 604/2 |
| 3,786,814 | 1/1974 | Armao | 128/303.1 |
| 4,082,096 | 4/1978 | Benson | 128/303.1 |
| 4,327,733 | 5/1982 | Gallie | 128/303.1 |
| 4,498,796 | 2/1985 | Gordon et al. | 604/3 |

FOREIGN PATENT DOCUMENTS 0639538 12/1978 U.S.S.R. ......................... 128/303.1

Primary Examiner—Max Hindenburg
Attorney, Agent, or Firm—Morton J. Rosenberg

[57] ABSTRACT

A cryogenic surgical tool (10) is provided to contact and freeze predetermined areas of tissue. The cryogenic surgical tool (10) consists of a low thermal conductivity handle (12) which is threadedly secured to an applicator member (20). The applicator member (20) includes an internal bore (26) within which is fitted an absorbent member (34) which absorbs a cryogenic liquid. The applicator member (20) includes an applicator first end surface (24) which contacts tissue and draws heat therefrom to extremely low temperatures, thus generally destroying the tissue contacted. The applicator member (20) includes a plurality of housing sidewall through openings (32) which are vent holes and allow for vaporization of the cryogenic liquid from the absorbent member (34) and prevents undue pressures from building up a cavity formed by bore (26) within housing member (20).

18 Claims, 1 Drawing Sheet

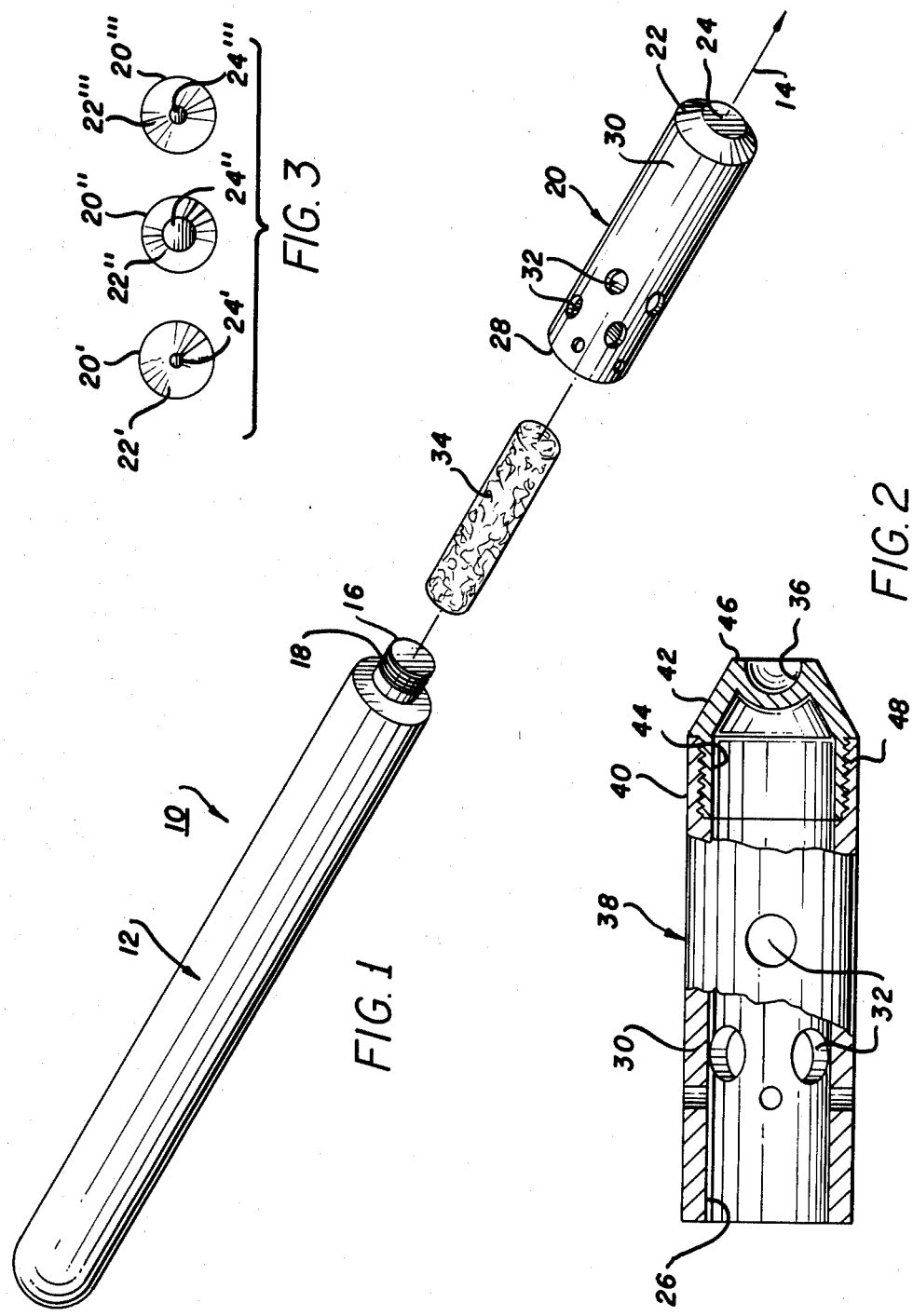

CRYOGENIC SURGICAL TOOL

BACKGROUND OF THE INVENTION

1. Field of the Invention

This invention pertains to a cryogenic surgical tool that is used specifically in dermatology for freezing benign and malignant lesions. The cryogenic surgical tool is used in cryosurgery which is one method for removing lesions by destroying tissue through a rapid reduction of temperature having a resulting tissue destruction. In particular, this invention relates to a cryogenic surgical tool where an absorbent member absorbs cryogenic liquid and is then inserted within a housing member. Further, this invention directs itself to a cryogenic surgical tool wherein a low conthermal conductivity handle member is threadedly secured to a housing member within which is captured an absorbent member having cryogenic liquid contained therein.

2. Prior Art

Cryogenic surgical tools adapted for cryosurgery are well-known in the art. In some prior art cryosurgery, Q-tips having a cotton ball that is rolled on the tip are dipped in liquid nitrogen. Such prior art methods of cryosurgery are deficient in that the diameter between one tip and another differs greatly and there is a lack of consistency as to the diameter of the diameter tip being applied to tissue.

In other prior art, pressurized canisters are used that release a cryogenic spray which touches the lesion on the mammalian body. In such prior art systems, spray tips have various sizes and are not easily controlled in the spray area. Generally, such prior art systems necessitate large canisters which have a tendency of psychologically impairing the patient prior to the cryosurgery.

The best prior art known to the Applicants include U.S. Pat. Nos. 4,327,733; 3,455,304; 3,434,477; 3,421,508; 3,736,937; 3,827,436; 3,259,131; 4,345,598; 4,377,168; 3,532,094; 3,702,114; 3,739,956; 3,736,936; 3,736,769; 3,794,039; 3,618,610; 4,457,308; 4,201,319; 4,207,897; and, 4,528,979.

In some prior art systems such as that shown in U.S. Pat. No. 4,327,733 there is provided a cryoenucleation tool having a spoon with a handle and a bowl. A loop is positioned to surround a tumor and liquid nitrogen flows through a coupling into the end of the tubing and around through the loop and then through an end portion to vent to the atmosphere. Such systems do provide for a tool which contiguously contacts a portion of the patient's body with liquid nitrogen passing around however, such utilizes a flowing mass of liquid nitrogen and does not provide for a simple easily dipped absorbent material within which coolant is applied and then capped for contiguous interface with the user's body.

In other prior systems such as U.S. Pat. No. 3,455,304, there are provided cryoextractors which have a thermally conducting cryoextractor tip mounted in one end of a casing and extending therefrom for interface with a patient's surface tissue. However, such systems do not provide for absorbent material which is the main heat transfer device of the subject concept.

SUMMARY OF THE INVENTION

A cryogenic surgical tool for substantially freezing predetermined areas of a mammalian body which includes a handle member adapted to be grasped by a user. Additionally, the cryogenic surgical tool includes an applicator member which is releasably secured to the handle member. The applicator member is adapted to contain a cryogenic liquid and an applicator first end having a first end surface for contiguous contact with the mammalian body.

BRIEF DESCRIPTION OF THE DRAWINGS

FIG. 1 is a perspective exploded view of the cryogenic surgical tool;

FIG. 2 is an embodiment of the cryogenic surgical tool showing a housing member threadedly secured to a tip housing; and, FIG. 3 is an end view of a plurality of housing members showing differing sized end surfaces for contacting tissue on the mammalian body.

DESCRIPTION OF THE PREFERRED EMBODIMENTS

Referring now to FIGS. 1-3, there is shown cryogenic surgical tool 10 used specifically in dermatology for freezing benign and malignant lesions. Cryogenic surgical tool 10 is particularly adapted to the area of surgery commonly referred to as cryosurgery which is one method for removal of lesions by substantially reducing the temperature of tissue on a mammalian body to a point where there is tissue destruction.

In overall concept, cryosurgery provides the surgical method of destroying tissue without utilization of a scalpel blade, thus providing a less likely probability of leaving a scar. Additionally, it has been found that in many instances, healing is attained without the leaving of a scar. The use of cryogenic surgical tool 10 further reduces the need for anesthesia and further through the rapid heat loss of the skin surface, the cold induces some reduction of pain by causing some local anesthesia.

Cryogenic surgical tool 10 includes handle member 12 which is shown in FIG. 1 to be extended in longitudinal direction 14. Handle member 12 is adapted to be grasped in the hand of a user and is generally formed of a low thermal conductivity material composition. In particular, handle member 12 may be formed of a plastic type composition not important to the inventive concept as herein described with the exception that such have a low thermal conductivity in order that such may be grasped comfortably by a user when applying cryogenic surgical tool 10 to predetermined surface areas of a mammalian body.

Handle member 12 further includes handle end section 16 including handle end section threads 18 for purposes to be described in following paragraphs. Handle member 12 may be solid, hollow, or a combination thereof.

Cryogenic surgical tool 10 further includes applicator member 20 which is releasably secured to handle member 12. Applicator member 20 is adapted to contain a cryogenic liquid such as liquid nitrogen and includes applicator first end 22 having first end surface 24 for contiguous contact to the mammalian body. Applicator member 20 defines a housing member which extends in longitudinal direction 14. Housing member or applicator 20 includes central bore 26 which is clearly shown in FIG. 2. Applicator or housing member 20 further includes second end 28 which is releasably secured to handle member 12 by way of threads (not shown) formed on an inner wall defined by central bore 26. In this manner, applicator or housing member 20 may be fixedly secured to handle member 12 through threaded securement and releasable therefrom in a reversible manner.

Housing member 20 includes housing sidewalls 30 having at least one through opening 32 passing therethrough into central bore 26 defining a housing cavity. Thus, housing member 20 forms a closed cylinder having openings in sidewalls 30 to define a recess therein for purposes to be described in following paragraphs.

Referring now to FIG. 3, there is shown end views of separate housing members 20', 20", and 20'". The overall structure of housing members 20', 20", and 20'" is equivalent to previously described housing member 20, however, such are provided with differing applicator first ends 22', 22", and 22'", which are chamfered at differing angles. The differing angles of inclination of first ends 22', 22", and 22'", provide for applicator first end surfaces 24', 24", and 24'" of differing diameters. Thus, appropriate diameters for differing sized lesions may be used in connection with removable housing members 20', 20", and 20'".

In this manner, a singular handle member 12 may be releasably secured to a plurality of housing members 20, 20', 20", or 20'", depending upon the diameter or surface area of a lesion to be contacted. Although not important to the inventive concept as herein described, first end surfaces may be formed with diameters of 2.0, 4.0, 6.0, 8.0, and 10.0 millimeters. Thus, a kit containing cryogenic surgical tool 10 may include a singular handle member 12 and a plurality of applicator members 20, 20', 20", and 20'".

Referring now to FIG. 1, it is seen that surgical tool 10 includes absorbent member 34 which may be cylindrical in contour as is shown, having an external diameter substantially equal to, but slightly smaller than, the diameter of central bore 26 of housing 20. Absorbent member 34 may be formed of a fibrous material composition such as cotton or some like material. The important consideration being that absorbent member 34 is able to absorb substantial quantities of a cryogenic liquid inserted therein for defining a self contained reservoir.

Thus, the user may either dip absorbent member 34 into a cryogenic liquid, or in the alternative, spray such liquid onto the surface of absorbent member 34. Absorbent member 34 is inserted within housing member 20 within bore 26. Subsequently, handle member 12 is threadedly secured to housing member 20 capturing fibrous absorbent member 34 therein. Openings 32 allow for the liquid cryogen to escape to the external atmosphere upon boiling, thus relieving undue pressures within housing member 20.

Housing member 30 is generally formed of a high thermal conductivity material composition and has successfully been used when housing member 20 is formed of a brass alloy. Additionally, housing member 20 may be formed of aluminum, copper, bronze, or some combination alloy with the only restriction being that it be substantially a high thermal conductivity composition to allow for heat transfer between the contacted lesion and the cryogenic temperatures formed within housing members 20 to provide a rapid heat transfer from the lesion.

Applicator member first end 22 as has been stated is chamfered at a predetermined angle to provide differing diameters of first end surfaces 24. Additionally, as is seen in FIG. 1, applicator first end surface 24 may be planar in contour thus providing a flat surface for contiguous interface with a lesion. Alternatively, as will be described for the embodiment shown in FIG. 2, first end 22 may include a semispherical contour of differing diameters defining semispherical interior surface 36 for contacting a skin surface. In this manner, semispherical inner surface 36 may surround a lesion which generally is hemispherical in contour and thus provides for contact of a greater area of the tissue being destroyed.

Referring now to FIG. 2, there is shown an embodiment of cryogenic tool 10 which includes open ended housing member 38 extended in longitudinal direction 14 having central through bore 26 extending therethrough in longitudinal direction 14. Open ended housing member 38 includes first end 40 which is releasably secured to tip housing 42 which includes second end 44 releasably secured to housing 38 on first end 40 as is shown. Tip housing 42 includes first end 46 which is adapted for contacting a lesion or other tissue on a mammalian body within concave inner surface 36.

Open ended housing member 38 includes housing sidewalls 30 and openings 32 as has been previously described for housing member 20 shown and described in FIG. 1. In FIG. 2, tip housing 42 is threadedly secured to open ended housing member 38 through mating engagement of threads 48 as is shown.

Absorbent members 34 may be inserted within bores 26 of open ended housing members 38, as has previously been described for housing member 20. Additionally, the identical type of attachment of handle 12 may be provided for open ended housing member 38 as was provided for housing member 20. In the embodiment shown in FIG. 2, a plurality of tip housings 42 may be easily attached and removed from open ended housing member 38 to provide differing sizes of semi-spherical inner surfaces 36 or in the alternative, differing planar contoured end surfaces such as 24', 24", and 24'", as is shown in FIG. 3.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A cryogenic surgical tool for substantially freezing predetermined areas of a mammalian body, comprising:
   (a) handle means adapted to be grasped by a user; and,
   (b) applicator means releasably secured to said handle means, said applicator means includes a housing member extended in a longitudinal direction, said housing member including a central bore forming a housing cavity extending in said longitudinal direction, said applicator means further including absorbent means inserted within said housing cavity, said absorbent means defining a self contained reservoir for maintaining a predetermined quantity of cryogenic liquid previously inserted therein, said housing member including an applicator first end having a first end surface for contiguous contact to said mammalian body, and a second end surface on the opposing side of said first end surface for contiguous contact with said absorbent means for rapidly removing heat therefrom, said applicator first end is chamfered at a predetermined inclination angle to provide for a predetermined diameter of said first end surface, said first end surface being a semi-spherical interior surface formed in said applicator first end, whereby said applicator means rapidly removes heat from said predetermined areas of said mammalian body subsequent to contiguous contact therewith.

2. The cryogenic surgical tool as recited in claim 1 where said housing member including a second end being releasably secured to said handle means.

3. The cryogenic surgical tool as recited in claim 2 where said housing member is threadedly secured to said handle means.

4. The cryogenic surgical tool as recited in claim 3 where said housing member includes housing sidewalls having at least one through opening passing therethrough into said central bore.

5. The cryogenic surgical tool as recited in claim 4 where said absorbent means is a fibrous material composition.

6. The cryogenic surgical tool as recited in claim 5 where said absorbent means is a cotton material composition.

7. The cryogenic surgical tool as recited in claim 4 where said housing member is formed of a high thermal conductivity material composition.

8. The cryogenic surgical tool as recited in claim 7 where said housing member is formed of brass.

9. The cryogenic surgical tool as recited in claim 1 where said handle means defines an elongated handle member to be grasped by a hand of a user.

10. The cryogenic surgical tool as recited in claim 9 where said handle member is formed of a low thermal conductivity material composition.

11. The cryogenic surgical tool as recited in claim 10 where said handle member is formed of a plastic composition.

12. A cryogenic surgical tool system for substantially freezing predetermined areas of a mammalian body comprising:
  (a) housing means extended in a longitudinal direction for containing a cryogenic liquid, said housing means having a central through bore extending therethrough in said longitudinal direction, said housing means includes absorbent means inserted within said housing means central through bore for defining a self contained reservoir for maintaining a predetermined quantity of said cryogenic liquid previously inserted therein;
  (b) applicator means releasably coupled to said housing means for contacting and subsequently substantially freezing said predetermined areas of said mammalian body, said applicator means includes a plurality of housing tips each of which is interchangeably releasably secured to said housing means, each of said housing tips including a first end and a second end; said first end including a first surface having an interior semi-spherical surface formed therein of predetermined dimensions, said predetermined dimensions being different for each of said housing tips, each of said housing tips includes a first end second surface on the opposing side of said first end first surface for contiguous contact with said absorbent means for rapidly removing heat therefrom; and,
  (c) handle means for grasping said cryogenic surgical tool system, said handle means being releasably coupled to said housing means, said handle means being formed of a low thermal conductivity material composition, whereby said applicator means rapidly removes heat from said predetermined areas of said mammalian body subsequent to contiguous contact therewith.

13. The cryogenic surgical tool system as recited in claim 12 where said second end of each of said housing tips are threadedly secured to said housing means on a first end thereof.

14. The cryogenic surgical tool system as recited in claim 12 where said housing means is threadedly secured to said handle means.

15. The cryogenic surgical tool system as recited in claim 12 where said housing means includes housing sidewalls having at least one through opening passing therethrough into said central bore.

16. The cryogenic surgical tool system as recited in claim 12 where said applicator means further includes at least one housing tip wherein said first surface of said first end includes a planar surface having a substantially planar contour of predetermined dimensions for contiguous interface with said mammalian body.

17. The cryogenic surgical tool system as recited in claim 16 where said planar end surface of said housing tip first end is substantially circular in contour.

18. The cryogenic surgical tool system as recited in claim 12 where each of said plurality of housing tips includes a tip housing recess for insert therein of at least a portion of a cryogenic liquid absorbent member.

* * * * *